(12) United States Patent
Adden et al.

(10) Patent No.: US 9,757,465 B2
(45) Date of Patent: *Sep. 12, 2017

(54) COMPOSITION COMPRISING AN ORGANIC DILUENT AND A CELLULOSE ETHER

(71) Applicant: Dow Global Technologies LLC, Midland, MI (US)

(72) Inventors: Roland Adden, Walsrode (DE); Robert L. Sammler, Midland, MI (US); Meinolf Brackhagen, Walsrode (DE); Nicholas S. Grasman, Midland, MA (US); Oliver Petermann, Hamburg (DE); Steven J. Guillaudeu, Midland, MI (US)

(73) Assignee: Dow Global Technologies LLC

( * ) Notice: Subject to any disclaimer, the term of this patent is extended or adjusted under 35 U.S.C. 154(b) by 91 days.

This patent is subject to a terminal disclaimer.

(21) Appl. No.: 14/390,049

(22) PCT Filed: Apr. 8, 2013

(86) PCT No.: PCT/US2013/035592
§ 371 (c)(1),
(2) Date: Oct. 2, 2014

(87) PCT Pub. No.: WO2013/154980
PCT Pub. Date: Oct. 17, 2013

(65) Prior Publication Data
US 2015/0065548 A1  Mar. 5, 2015

Related U.S. Application Data

(60) Provisional application No. 61/622,757, filed on Apr. 11, 2012.

(51) Int. Cl.
| | | |
|---|---|---|
| *A01N 43/50* | (2006.01) | |
| *A61K 31/415* | (2006.01) | |
| *A61K 47/38* | (2006.01) | |
| *A61K 9/08* | (2006.01) | |
| *C08B 11/193* | (2006.01) | |
| *C08B 11/20* | (2006.01) | |
| *C09D 101/28* | (2006.01) | |
| *C08L 1/28* | (2006.01) | |
| *A61K 9/16* | (2006.01) | |
| *A61K 31/343* | (2006.01) | |
| *A61K 31/4166* | (2006.01) | |
| *A61K 47/10* | (2017.01) | |

(52) U.S. Cl.
CPC ............... *A61K 47/38* (2013.01); *A61K 9/08* (2013.01); *A61K 9/16* (2013.01); *A61K 9/1617* (2013.01); *A61K 9/1652* (2013.01); *A61K 31/343* (2013.01); *A61K 31/4166* (2013.01); *A61K 47/10* (2013.01); *C08B 11/193* (2013.01); *C08B 11/20* (2013.01); *C08L 1/28* (2013.01); *C08L 1/284* (2013.01); *C09D 101/28* (2013.01); *C09D 101/284* (2013.01)

(58) Field of Classification Search
None
See application file for complete search history.

(56) References Cited

U.S. PATENT DOCUMENTS

| | | | |
|---|---|---|---|
| 2,613,142 A | 10/1952 | Wiezer | |
| 3,477,864 A | 11/1969 | Tuji | |
| 3,493,407 A | 2/1970 | Greminger, Jr. et al. | |
| 4,316,982 A | 2/1982 | Holst et al. | |
| 6,235,893 B1 * | 5/2001 | Reibert | C08B 11/02 264/140 |
| 7,666,918 B2 | 2/2010 | Prieto et al. | |
| 2013/0236512 A1 * | 9/2013 | Adden | C08B 11/193 424/400 |
| 2014/0093561 A1 * | 4/2014 | Chen | A61K 9/1617 424/456 |

FOREIGN PATENT DOCUMENTS

| | | | |
|---|---|---|---|
| EP | 0210917 A2 | 2/1987 | |
| EP | 0240773 A1 | 10/1987 | |
| EP | 0872233 A1 | 10/1998 | |
| EP | 1141029 B1 * | 5/2003 | C08B 11/20 |
| EP | 1423433 B1 | 3/2007 | |

(Continued)

OTHER PUBLICATIONS

The Dow Technical Handbook (METHOCEL Cellulose Eithers; 2002).*
J. of Drug Targeting, 2010, 18(10), p. 704-731, Using polymeric precipitation inhibitors to improve the absorption of poorly-soluble drugs, Warren et al.
Int. J. of Pharm, 2001, 212, p. 213-221, Crystallization of hydrocortisone acetate, Raghavan et al.
Int. J.of Polymer Anal. Charact., 2009, 14, p. 617-630, Characterization of Hypromellose Acetate Succinate by Size Exclusion Chromatography, Chen.
Pharma. Research, 2009, vol. 26, No. 6, Utility of Hydroxypropylmethylcellulose Acetate Succinate, Curatolo et al.
Drug Discovery Today, 2011, xxx, No. xx, p. e1-e7, the use of amorphous solid dispersions, Van den Mooter.

(Continued)

*Primary Examiner* — Dennis Heyer
*Assistant Examiner* — Daniel M Podgorski

(57) ABSTRACT

A liquid composition comprises an organic diluent and at least one cellulose ether having anhydroglucose units joined by 1-4 linkages and having methyl groups, hydroxyalkyl groups, and optionally alkyl groups being different from methyl as substituents such that hydroxyl groups of anhydroglucose units are substituted with methyl groups such that $s_{23}/s_{26}$ is 0.29 or less, wherein $s_{23}$ is the molar fraction of anhydroglucose units wherein only the two hydroxyl groups in the 2- and 3-positions of the anhydroglucose unit are substituted with a methyl group and wherein $s_{26}$ is the molar fraction of anhydroglucose units wherein only the two hydroxyl groups in the 2- and 6-positions of the anhydroglucose unit are substituted with a methyl group. The liquid composition can be used for preparing a solid dispersion of an active ingredient in a cellulose ether.

17 Claims, No Drawings

(56) References Cited

FOREIGN PATENT DOCUMENTS

| WO | 0185135 | A1 | 11/2001 |
| WO | 2005115330 | A2 | 12/2005 |
| WO | 2006090150 | A1 | 8/2006 |
| WO | 2008047201 | A2 | 4/2008 |

OTHER PUBLICATIONS

J. Chem.Inf.Comput.Sci., 1987, 27, p. 21-35, Atomic Physicochemical Parameters for Three-Dimensional-Structure Directed Quantitative Structure-Activity Relationships, Ghose et al.

J. Chem.Inf.Comput.Sci., 1989, 29, p. 163-172, Atomic Physicochemical Parameters for Three Dimensional Structure Directed Quantitative Structure-Activity Relationships, Viswanadhan et al.

Eur. J.Med.Chem.-Chim., 1984, 19, No. 1, p. 71-78, Molecular structures, Broto et al.

Eur. J.of Pharma. and Biopharm., 2002, 54, p. 107-117, Melt extrusion, Breitenbach.

Carb. Research, 1988, 176, p. 137-144, Distribution of Substituents in O-Ethyl-O(2-Hydroxyethyl) Cellulose, Lindberg et al.

J. of Gas Chrom., 1964, p. 173-179, Fundamental Groups in the Response of Flame Ionization Detectors to Oxygenated Aliphatic Hydrocarbons, Ackman.

J. of Gas Chrom., 1968, vol. 6, p. 135-138, Flame Ionization Detector Molar Resonses for Methyl Esters of Some Polyfunctional Metabolic Acids, Addison et al.

Carb. Research, 1975, 40, p. 217-225, Quantitative Analysis by various G.L.C. Respons-Factor Theories, Sweet et al.

Mol. Pharma., 2008, vol. 5, No. 6, Hydroxypropyl Methylcellulose Acetate Succinate, Friesen et al.

ASTM, D2363-79, (Reapproved 2006), Standard Test for Methods for Hydroxypropyl Methylcellulose.

J. of Pharma. Sci., 2008, vol. 97, No. 8, Process Induced Disorder in Crystalline Materials, Feng et al.

Mol. Pharma., 2011, 8, p. 564-570, Excipient-Mediated Supersaturation Stabilization in Human Intestinal Fluids, Bevernage et al.

* cited by examiner

COMPOSITION COMPRISING AN ORGANIC DILUENT AND A CELLULOSE ETHER

FIELD

This invention relates to a liquid composition comprising an organic diluent and a cellulose ether and to solid dispersions of an active ingredient in a cellulose ether.

INTRODUCTION

A large number of presently known drugs have a low solubility in water, so that complex techniques are required to prepare a dosage form. Much research is spent on the use of pharmaceutically acceptable water-soluble polymers in combination with drugs of low water solubility. The use of water-soluble polymers aims at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion. However, simple blending of a water-soluble polymer with a drug of low water solubility generally does not reduce the crystallinity of the drug.

G. Van den Mooter, "The use of amorphous solid dispersions: A formulation strategy to overcome poor solubility and dissolution rate", *Drug Discov Today: Technol* (2011), doi:10.1016/j.ddtec.2011.10.002, discusses the preparation of amorphous solid dispersions to increase the bioavailability of poorly soluble drugs by improving their rate and extent of dissolution. The two most applied manufacturing methods for preparing amorphous solid dispersions are said to be spray drying and hot melt extrusion. The former process starts from a solution of the drug and a carrier in a common organic solvent or mixture of solvents. This solution is atomized using a nozzle and the solvent is subsequently quickly evaporated (order of magnitude is milliseconds). The very fast solvent evaporation contributes to the amorphous state of the solid dispersion.

Dallas B. Warren et al. (*Journal of Drug Targeting*, 2010; 18(10): 704-731) have studied the use of water-soluble cellulose ethers as polymeric precipitation inhibitors, such carboxymethyl cellulose (CMC), methyl cellulose (MC), hydroxyethyl cellulose (HEC), and hydroxypropylmethyl cellulose (HPMC) to improve the absorption of poorly water-soluble drugs.

S. L. Raghavan et al. (International Journal of Pharmaceutics 212 (2001) 213-221), have studied the influence of hydroxypropyl methylcellulose (HPMC), methylcellulose (MC), polyvinyl pyrrolidone (PVP) and polyethylene glycol (PEG400) on the crystallization of hydrocortisone acetate (HA).

International Patent Application WO 01/85135 discloses an itraconazole-containing pharmaceutical composition, obtained by spray-drying a solution in which an itraconazole and a pH-independent water-soluble polymer are dissolved into a solvent. WO 01/85135 teaches that the spraying-drying of itraconazole with the water-soluble polymer improves the solubility of itraconazole into water and its pharmaceutical efficacy. Among other water-soluble polymers WO 01/85135 suggests the use of cellulose derivatives, such as methylcellulose, ethylcellulose, hydroxypropyl cellulose, hydroxyethyl cellulose, hydroxyethyl methylcellulose, hydroxypropyl methylcellulose, carboxymethyl cellulose, sodium carboxymethyl cellulose, and carboxymethyl ethylcellulose. Methylcellulose, hydroxypropyl methylcellulose, and hydroxypropyl cellulose are said to remarkably increase the water solubility of itraconazole.

International Patent Application WO2008/047201 discloses solid dispersions which comprise a poorly water soluble ionizable drug, a cationic species, and a dispersion polymer, such as hydroxypropyl methylcellulose (HPMC). According to the examples a drug and HPMC (E3 Prem LV; Methocel®, available from The Dow Chemical Company, Midland, Mich.) are mixed with water and methanol to form spray solutions. Solid spray-dried dispersions of the drug in HPMC are produced.

In view of the high importance and large number of poorly water soluble drugs, it is an object of the present invention to provide new liquid compositions, which comprise an organic diluent and a cellulose ether, into which active ingredients can be incorporated, such as poorly water-soluble drugs, and which can be spray-dried to produce solid dispersions of the active ingredient in the cellulose ether. It is a preferred object of the present invention to provide new liquid compositions from which improved spray-dried solid dispersions of an active ingredient in a cellulose ether can be produced. It is another preferred object of the present invention to find new solid dispersions of an active ingredient in a cellulose ether which are able to improve the aqueous solubility of the active ingredient to a larger extent than known hydroxypropyl methylcelluloses.

SUMMARY

Surprisingly, it has been found that the aqueous solubility of an active ingredient can be significantly improved by providing a solid dispersion of the active ingredient in a cellulose ether if a cellulose ether is chosen wherein the ether substituents have a specific distribution pattern.

Accordingly, one aspect of the present invention is a liquid composition which comprises an organic diluent and at least one cellulose ether having anhydroglucose units joined by 1-4 linkages and having methyl groups, hydroxyalkyl groups, and optionally alkyl groups being different from methyl as substituents such that hydroxyl groups of anhydroglucose units are substituted with methyl groups such that $s23/s26$ is 0.29 or less, wherein $s23$ is the molar fraction of anhydroglucose units wherein only the two hydroxyl groups in the 2- and 3-positions of the anhydroglucose unit are substituted with a methyl group and wherein $s26$ is the molar fraction of anhydroglucose units wherein only the two hydroxyl groups in the 2- and 6-positions of the anhydroglucose unit are substituted with a methyl group.

Another aspect of the present invention is the use of the liquid composition as defined above for preparing a solid dispersion of at least one active ingredient in at least one cellulose ether.

Yet another aspect of the present invention is a solid dispersion of at least one active ingredient in at least one cellulose ether, wherein the cellulose ether is as defined above.

Yet another aspect of the present invention is a process for coating a dosage form which comprises the step of contacting the liquid composition as defined above with the dosage form.

Yet another aspect of the present invention is a process for the manufacture of capsules comprising the step of contacting the liquid composition as defined above with dipping pins.

DETAILED DESCRIPTION

The liquid composition of the present invention comprises at least one cellulose ether, which has anhydroglucose units joined by 1-4 linkages and which has methyl groups, hydroxyalkyl groups, and optionally alkyl groups being different from methyl as substituents. The hydroxyalkyl groups can be the same or different from each other. Preferably the cellulose ether comprises one or two kinds of hydroxyalkyl groups, more preferably one or more kinds of hydroxy-$C_{1-3}$-alkyl groups, such as hydroxypropyl and/or hydroxyethyl. Useful optional alkyl groups are, e.g., ethyl or propyl, ethyl being preferred. Preferred ternary cellulose ethers are ethyl hydroxypropyl methyl celluloses, ethyl hydroxyethyl methyl celluloses, or hydroxyethyl hydroxypropyl methyl celluloses. Preferred cellulose ethers are hydroxyalkyl methyl celluloses, particularly hydroxy-$C_{1-3}$-alkyl methyl celluloses, such as hydroxypropyl methylcelluloses or hydroxyethyl methylcelluloses.

An essential feature of the cellulose ether is its unique distribution of methyl groups on the anhydroglucose units such that s23/s26 is 0.29 or less, preferably 0.28 or less, more preferably 0.26 or less, most preferably 0.24 or less, and particularly 0.22 or less. Typically s23/s26 is 0.05 or more, more typically 0.08 or more, and most typically 0.11 or more.

In the ratio s23/s26, s23 is the molar fraction of anhydroglucose units wherein only the two hydroxyl groups in the 2- and 3-positions of the anhydroglucose unit are substituted with methyl groups and s26 is the molar fraction of anhydroglucose units wherein only the two hydroxyl groups in the 2- and 6-positions of the anhydroglucose unit are substituted with methyl groups. For determining the s23, the term "the molar fraction of anhydroglucose units wherein only the two hydroxyl groups in the 2- and 3-positions of the anhydroglucose unit are substituted with methyl groups" means that the 6-positions are not substituted with methyl; for example, they can be unsubstituted hydroxyl groups or they can be substituted with hydroxyalkyl groups, methylated hydroxyalkyl groups, alkyl groups different from methyl or alkylated hydroxyalkyl groups. For determining the s26, the term "the molar fraction of anhydroglucose units wherein only the two hydroxyl groups in the 2- and 6-positions of the anhydroglucose unit are substituted with methyl groups" means that the 3-positions are not substituted with methyl; for example, they can be unsubstituted hydroxyl groups or they can be substituted with hydroxyalkyl groups, methylated hydroxyalkyl groups, alkyl groups different from methyl or alkylated hydroxyalkyl groups.

The term "hydroxyl group substituted with methyl group" or "hydroxyl group substituted with hydroxyalkyl group" as used herein means that the hydrogen atom on the hydroxyl group is replaced by a methyl group or a hydroxyalkyl group.

Formula I below illustrates the numbering of the hydroxyl groups in anhydroglucose units. Formula I is only used for illustrative purposes and does not represent the cellulose ethers of the invention; the substitution with hydroxyalkyl groups is not shown in Formula I.

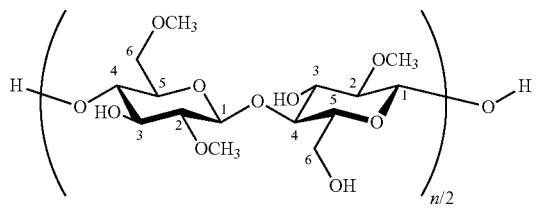

Formula I

The cellulose ether preferably has a DS(methyl) of from 1.6 to 2.5, more preferably from 1.7 to 2.4, and most preferably from 1.7 to 2.2. The degree of the methyl substitution, DS(methyl), of a cellulose ether is the average number of OH groups substituted with methyl groups per anhydroglucose unit. For determining the DS(methyl), the term "OH groups substituted with methyl groups" does not only include the methylated OH groups directly bound to the carbon atoms of the cellulose backbone but also methylated OH groups that have been formed after hydroxyalkylation.

The cellulose ether generally has an MS (hydroxyalkyl) of 0.05 to 0.55, preferably 0.07 to 0.50, more preferably 0.10 to 0.45, and most preferably 0.15 to 0.35. The degree of the hydroxyalkyl substitution is described by the MS (molar substitution). The MS (hydroxyalkyl) is the average number of hydroxyalkyl groups which are bound by an ether bond per mole of anhydroglucose unit. During the hydroxyalkylation, multiple substitutions can result in side chains.

The sum of the MS (hydroxyalkyl) and the DS(methyl) preferably is at least 1.8, more preferably at least 1.9, and preferably up to 2.7, more preferably up to 2.5.

The determination of the % methoxyl and % hydroxypropoxyl in hydroxypropyl methylcellulose is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion.

The viscosity of the cellulose ether utilized in the liquid composition of the present invention generally is from 2.4 to 200 mPa·s, preferably from 2.4 to 100 mPa·s, more preferably from 2.5 to 50 mPa·s, and in particular from 3 to 30 mPa·s, measured as a 2 weight-% aqueous solution at 20° C. according to ASTM D2363-79 (Reapproved 2006).

Methods of making the above described cellulose ethers are described in detail in the Examples. Some aspects of the process for making the cellulose ethers are described in more general terms below.

The cellulose ether described above can be obtained by a multistage etherification process comprising:
  a first stage comprising:
    i. treating cellulose pulp with a first amount of alkalizing agent, and
    ii. addition of at least one methylating agent to the cellulose pulp, subsequent heating of the reaction mixture to a reaction temperature of 70° C. or more and thereafter
  at least one additional stage comprising:
    iii. addition of an additional amount of alkalizing agent to the reaction mixture at a rate of less than 0.075 molar equivalents of alkalizing agent per mole of anhydroglucose units per minute at a temperature of at least 65° C., and, optionally for each individual additional stage, iv. addition of an additional amount of at least one methylating agent to the reaction mixture, wherein before, after or concurrently with the addition of the alkalizing agent in the first stage at least one hydroxyalkylating agent, and optionally at least one alkylation agent different from a methylating agent, is added to the cellulose pulp, or, as the etherification of the cellulose pulp proceeds, to the partially reacted cellulose pulp.

The cellulose raw material for preparing the cellulose ether is typically cellulose pulp obtained from cotton or wood, preferably wood pulp. It is typically provided in powder or chip form.

In the above-mentioned process the cellulose pulp or, as the reaction of cellulose pulp to the hydroxyalkyl methyl cellulose proceeds, the partially reacted cellulose pulp, is alkalized in two or more stages, preferably in two or three stages, in one or more reactors with an alkalizing agent. The alkalizing agent may be any strong base such as an alkali metal hydroxide, preferably sodium hydroxide, caustic soda or lime or a mixture of more than one of such strong bases, employed as an aqueous solution. Usually an aqueous solution of an alkali metal hydroxide is employed, preferably having an alkali metal hydroxide content of from 30 to 70 percent, more preferably from 35 to 60 percent, most preferably from 48 to 52 percent, based on the total weight of the aqueous solution of the alkali metal hydroxide.

In one embodiment, an organic solvent such as dimethyl ether is added to the reactor as a diluent and a coolant. Likewise, the headspace of the reactor is optionally purged with an inert gas (such as nitrogen) to control oxygen-catalyzed depolymerization of the cellulose ether product.

In the first stage of the process the cellulose pulp is treated with a first amount of alkalizing agent, typically from 1.2 to 3.5 molar equivalents of alkalizing agent per mole of anhydroglucose units in the cellulose. The treatment can be conducted by any means known in the art such as by steeping in a bath or stirred tank or spraying. Uniform swelling and distribution of the alkalizing agent in the pulp may be achieved by mixing and agitation. In the first stage the rate of addition of the aqueous solution of the alkalizing agent to the cellulose pulp is not critical. It may be added in several portions, e.g. 2 to 4 portions, or continuously. During first stage alkalization, which usually lasts from 15 to 60 minutes, the temperature is typically maintained at 45° C. or below.

Moreover, a methylating agent such as methyl chloride or dimethyl sulfate is added to the cellulose pulp within the first stage of the process, before, after or concurrently with the first amount of alkalizing agent, preferably after the addition of the alkalizing agent. The methylating agent can be added to the cellulose or, as the reaction of cellulose pulp to the hydroxyalkyl methyl cellulose proceeds, to partially reacted cellulose pulp, in a single stage, but it is preferably added in two or more stages, more preferably two or three stages, most preferably two stages.

If the methylating agent is added in a single stage, it is generally added in an amount of from 3.5 to 6.0 mole of methylating agent per mole of anhydroglucose units, but in any event it is added in at least an equimolar amount, compared to the alkalizing agent added in the first stage, before heating the reaction mixture. If the methylating agent is added in a single stage, it is preferably added at a rate of from 0.25 to 1.0 molar equivalents of methylating agent per mole of anhydroglucose units per minute. The methylating agent used in the first stage may be pre-mixed with any conventional suspending agent. In this case, a mixture comprising from 20 to 50%, more preferably from 30 to 50%, of the suspending agent, based on the total weight of the suspending agent and the at least one methylating agent is preferably employed.

Once the cellulose has been treated with the first amount of alkalizing agent and the additions of the methylating agent and possible further components of the first stage, preferably conducted also at a temperature of 45° C. or below, have been accomplished, the reaction mixture is heated, typically within 30 to 80 minutes, to a reaction temperature of at least 70° C., preferably in the range of 70-90° C., more preferably in the range of 70-80° C. Usually the reaction is then allowed to proceed at this reaction temperature for 10 to 30 minutes.

Subsequently the process comprises at least one additional stage comprising addition of an additional amount of alkalizing agent and, optionally for each individual additional stage, addition of an additional amount of the methylating agent to the reaction mixture. The total amount of additional alkalizing agent added as aqueous solution within the at least one additional stage typically ranges from 1.0 to 2.9 molar equivalents of alkalizing agent per mole of anhydroglucose units. Preferably, the molar equivalent ratio between the amount of alkalizing agent added in the first stage and the amount of alkalizing agent added in total in the at least one additional stage is from 0.6:1 to 3.5:1. It is important to add the alkalizing agent in the at least one additional stage slowly to the reaction mixture, i.e. at a rate of less than 0.075, preferably less than 0.065, more preferably less than 0.055 molar equivalents of alkalizing agent per mole of anhydroglucose units per minute. The alkalizing agent of the second stage is generally added at a temperature of from 65 to 85° C., preferably from 70 to 80° C.

Typically the methylating agent is used in a total amount in the range of 2 to 6 moles per mole of anhydroglucose units. If the methylating agent is added not only in the first stage, but also in at least one additional subsequent stage, preferably in one additional stage, it is typically added in an amount of 2.0 to 4.0 mole of methylating agent per mole of anhydroglucose units in the first stage and in a total amount of 1.5 to 3.4 mole of methylating agent per mole of anhydroglucose units in the at least one additional stages. In any event the methylating agent is added in at least an equimolar amount, compared to the alkalizing agent present in the reaction mixture. Accordingly, the methylating agent of the second stage, if any, is added to the reaction mixture before or during the second and optionally third stage of adding the alkalizing agent in such a manner that the cellulose or, as the reaction of cellulose pulp to the hydroxyalkyl methyl cellulose proceeds, the partially reacted cellulose pulp, is continuously contacted with an at least equimolar equivalent amount of the methylating agent compared to the alkalizing agent.

If the methylating agent is added in two stages, the methylating agent of the first stage is preferably added at a rate of from 0.25 to 0.5 molar equivalents of methylating agent per mole of anhydroglucose units per minute. The methylating agent of the single stage or of the first stage may be pre-mixed with a suspending agent. In this case the mixture of suspending agent and methylating agent preferably comprises from 20 to 50 weight percent, more preferably from 30 to 50 weight percent, of the suspending agent, based on the total weight of methylating agent and suspending agent.

If the methylating agent is added in two stages, the second stage of methylating agent is generally added to the reaction mixture after having heated the reaction mixture to a temperature of about 70-90° C. for 10 to 30 minutes. The methylating agent of the second stage is preferably added at a rate of from 0.25 to 0.5 molar equivalents of methylating agent per mole of anhydroglucose units per minute. If the methylating agent is added in two stages, the molar ratio between the methylating agent of the first stage and the methylating agent of the second stage is generally from 0.68:1 to 1.33:1. The methylating agent in each of the at least one additional stage, if used therein, should be added to the reaction mixture prior to or during the addition of the additional amount of alkalizing agent of that stage in such a manner that the cellulose is continuously contacted with an at least equimolar equivalent amount of the at least one methylating agent compared to the alkalizing agent.

As an alternative to the procedure described above wherein the methylating agent and alkalizing agent each are added in two stages, the methylating agent of the second stage may be added to the reaction mixture after a portion of the alkalizing agent of the second stage has been added, followed by subsequent addition of alkalizing agent; i.e., the methylating agent is added in a second stage, which is followed by the addition of a third stage alkalizing agent. In this embodiment of the process, the total amount of alkalizing agent per mole of anhydroglucose added in the second and third stage is generally 1.0 to 2.9 moles per mole of anhydroglucose units, of which preferably 40 to 60 percent are added in the second stage and 60 to 40 percent are added in the third stage. Preferably the alkalizing agent used in the third stage is added slowly, i.e., at a rate of less than 0.075, typically at a rate of less than 0.055 molar equivalents of alkalizing agent per mole of anhydroglucose units per minute. The methylating agent and alkalizing agent of the third stage are generally added at a temperature of from 65 to 85° C., preferably from 70 to 80° C.

One or more, preferably one or two, hydroxyalkylating agents, such as ethylene oxide and/or propylene oxide are also added to the cellulose pulp, or, as the reaction of cellulose pulp to the hydroxyalkyl methyl cellulose proceeds, to partially reacted cellulose pulp, either before, after, or concurrently with the alkalizing agent added in the first stage. A single hydroxyalkylating agent or more than one, preferably only one, hydroxyalkylating agent may be utilized. The hydroxyalkylating agent is generally added in an amount of 0.2 to 2.0 mole of hydroxyalkylating agent per mole of anhydroglucose units. The hydroxyalkylating agent is advantageously added before heating the reaction mixture to the reaction temperature, i.e. at a temperature of from 20 to 70° C., preferably from 40 to 60° C.

An additional alkylating agent, different from a methylating agent, may also be added to the cellulose pulp, either before, after, or concurrently with the alkalizing agent added in the first stage. Non-limiting examples include ethyl chloride, ethyl bromide or ethyl iodide, diethyl sulphate and/or propyl chloride. The additional alkylating agent is generally added in an amount of 0.5 to 6 mole of alkylating agent per mole of anhydroglucose units. The alkylating agent is advantageously added before heating the reaction mixture to the reaction temperature, i.e. at a temperature of from 20 to 70° C., preferably from 40 to 60° C.

After accomplishment of the above described multistage etherification the obtained cellulose ether is typically further purified, dried and/or milled. Usually the cellulose ether is washed to remove salt and other reaction by-products. Any solvent in which the salt formed as a by-product of the etherification reaction is soluble may be employed, but water is usually utilized. The cellulose ether may be washed in the reactor, but is preferably washed in a separate washer located downstream of the reactor. Before or after washing, the cellulose ether may be stripped e.g. by exposure to steam to reduce the content of residual volatile organic compounds.

The cellulose ether can be dried to reduce moisture and the content of other volatile compounds to preferably 0.5 to 10.0 wt. %, more preferably 0.8 to 5.0 wt. % of water and other volatile compounds, based on the sum of the weight of the cellulose ether, water and other volatile compounds. Drying can be carried out using a conventional drier such as a tray drier, fluid bed drier, flash drier, agitation drier or tube drier. The reduced moisture and content of other volatile compounds enables the cellulose ether to be milled into particulate form. The dried cellulose ether can be milled to particulates of desired size by any suitable means known in the art such as a ball mill, an impact pulverizer, knife grinder or air-swept impact mill. If desired, drying and milling can be conducted simultaneously.

According to the above-mentioned process a cellulose ether is obtained which generally has a viscosity of more than 150 mPa·s, preferably from 500 to 200,000 mPa·s, more preferably from 500 to 100,000 mPa·s, most preferably from 1,000 to 80,000, particularly from 1,000 to 60,000, determined in a 1.5% by weight aqueous solution at 20° C. in a Haake RS600 at a shear rate of 2.55 s$^{-1}$. For preparing a cellulose ether which is particularly suitable for use in the liquid composition of the present invention, such cellulose ether is generally subjected to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent. In such partial depolymerization process a cellulose ether can be obtained which has a viscosity of from 2.4 to 200 mPa·s, preferably from 2.4 to 100 mPa·s, more preferably from 2.5 to 50 mPa·s, in particular from 3 to 30 mPa·s, determined in a 2% by weight aqueous solution at 20° C. according to ASTM D2363-79 (Reapproved 2006).

The composition of the present invention is liquid at 25° C. and atmospheric pressure and comprises an organic diluent, in addition to at least one cellulose ether as described above. The term "organic diluent" as used herein means an organic solvent or a mixture of two or more organic solvents. Preferred organic diluents are polar organic solvents having one or more heteroatoms, such as oxygen, nitrogen or halogen like chlorine. More preferred organic diluents are alcohols, most preferably multifunctional alcohols, such as glycerol, or monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; nitriles, such as acetonitrile. More preferably the organic diluents have 1 to 6, most preferably 1 to 4 carbon atoms. The liquid composition of the present invention may additionally comprise water; however, the liquid composition should comprise more than 50, more preferably at least 65, and most preferably at least 75 weight percent of an organic diluent and less than 50, more preferably up to 35, and most preferably up to 25 weight percent of water, based on the total weight of the organic diluent and water. Specific examples of preferred organic diluents, optionally mixed with minor amounts of water are: methanol, tetrahydrofuran, methylene chloride, a blend of 80 to 95 weight percent of methanol and 20 to 5 weight percent of water, a blend of 80 to 95 weight percent of tetrahydrofuran and 20 to 5 weight percent of water, a blend of 55 to 85 weight percent of acetone and 45 to 15 weight percent of water, a blend of 15 to 85 weight percent of acetone and 85 to 15 weight percent of methanol, a blend of 15 to 85 weight percent of methyl ethyl ketone and 85 to 15 weight percent of methanol, a blend of 30 to 50 weight percent of acrylonitrile and 70 to 50 weight percent of a $C_{1-4}$-monoalcohol, such as methanol, ethanol, isopropylalcohol, or n-propanol; a blend of 30 to 50 weight percent of methanol and 70 to 50 weight percent of tetrahydrofuran or ethyl acetate, or a blend of 70 to 90 weight percent of ethanol and 10 to 30 weight percent of tetrahydrofuran or ethyl acetate.

The liquid composition of the present invention is useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the liquid composition of the present invention preferably comprises one or more active ingredients, most preferably one or more drugs. The term "drug" is conventional, denoting a compound having beneficial prophylactic and/or therapeutic properties when administered to an animal, especially humans. Preferably, the drug is a "low-solubility drug", meaning that the drug has a minimum aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than 0.1 mg/mL or less than 0.05 mg/mL or less than 0.02 mg/mL, or even less than 0.01 mg/mL where the aqueous solubility (mg/mL) is the minimum value observed in any physiologically relevant aqueous solution (e.g., those with pH values between 1 and 8) including USP simulated gastric and intestinal buffers.

The cellulose ethers comprised in the liquid compositions of the present invention and in the solid dispersions of the present invention are able to maintain the concentration of poorly water-soluble active ingredients, such as poorly water-soluble drugs in aqueous solutions at supersaturation levels. A considerably higher concentration of a poorly water-soluble active ingredient in an aqueous solution can be maintained than in the absence of a cellulose ether described above. The degree of supersaturation of a poorly water-soluble active ingredient in an aqueous solution depends on various factors, such as the physical stability and the dissolution rate of a given active ingredient. Dwayne T. Friesen et al. in MOLECULAR PHARMACEUTICS VOL. 5, NO. 6, 1003-1019, 2008 have classified compounds with a structurally diverse range of physicochemical properties on a physical property map Tm/Tg ratio versus log P. The log P value is a standard measure of the lipophilicity of a compound. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (27 J. Chem. Inf. Comput. Sci. 2 1 (1987)); Viswanadhan's fragmentation method (29 J. Chem. Inf. Comput. Sci. 163 (1989)); or Broto's fragmentation method (19 Eur. J. Med. Chem.-Chim Theor. 7 1 (1984)).

$$\log P_{oct/wat} = \log\left(\frac{[\text{solute}]_{octanol}}{[\text{solute}]_{water}^{un\text{-}ionized}}\right)$$

Compounds with high log P values are very hydrophobic and tend to have extremely low water solubilities (often less than 1 μg/mL when their melting points are above about 100° C.) and low propensities for wetting when placed into water.

Tm is the melting temperature and Tg is the glass transition temperature of the compound at atmospheric pressure. Dwayne T. Friesen et al. have divided the compounds into four groups based on their position on this physical property map Tm/Tg ratio versus log P (FIG. 14 on page 1018 in MOLECULAR PHARMACEUTICS VOL. 5, NO. 6, 2008). The first group, Group 1, consists of compounds with relatively low Tm/Tg ratios (<1.25 K/K) and low to moderate log P values (less than about 6); Compounds in Group 2 have somewhat higher Tm/Tg ratios (1.25-1.4) and low to moderate log P values (less than about 6). Compounds in Group 3 have even higher Tm/Tg values (greater than 1.4) and low to moderate log P values (less than about 6). Finally, Group 4 compounds have high log P values (at least about 6).

It has surprisingly been found that the cellulose ethers utilized in the liquid composition of the present invention even have a higher ability than known comparable cellulose ethers to keep some active ingredients at a supersaturation level in an aqueous solution. For example the drug Griseofulvin, which has a very low water solubility of 8.54 mg/l and belongs to group 2 on the map Tm/Tg ratio versus log P (FIG. 14 on page 1018 in MOLECULAR PHARMACEUTICS VOL. 5, NO. 6, 2008) has a higher concentration in the presence of an above-described cellulose ether wherein s23/s26 is 0.29 or less than in the presence of a comparable cellulose ether wherein s23/s26 is more than 0.29.

Accordingly, a preferred aspect of the present invention is a liquid composition or a solid dispersion which comprises at least one cellulose ether as described above and additionally at least one active ingredient that has a Tm/Tg ratio of more than 1.0 up to 1.8, preferably more than 1.1 up to 1.6, more preferably 1.15 up to 1.5, most preferably 1.25 to 1.40, wherein the melting temperature Tm and the glass transition temperature Tg each are in Kelvin. The active ingredient preferably has a log P of more than 1 up to 11, preferably 1.5 to 8, most preferably 2 to 6.

The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The liquid composition of the present invention preferably comprises from 1 to 40 weight percent, more preferably from 2.5 to 30 weight percent, most preferably from 5 to 25 weight percent, and particularly from 7 to 20 percent of at least one cellulose ether as described above, from 40 to 99 weight percent, more preferably from 54.9 to 97.4 weight percent, most preferably from 65 to 94.5 weight percent and particularly from 70 to 92 percent of an organic diluent, and from 0 to 40 percent, preferably from 0.1 to 40 percent, most preferably from 0.5 to 25 percent, and particularly from 1 to 15 percent of an active ingredient, based on the total weight of the liquid composition.

In one aspect of the invention the liquid composition of the present invention comprising at least one cellulose ether as described above, one or more active ingredients and optionally one or more adjuvants can be used in liquid form, for example in the form of a suspension, a sprayable composition, or a syrup. The liquid composition is useful, e.g., for oral, ocular, topical, rectal or nasal applications. The liquid diluent should generally be pharmaceutically acceptable, such as ethanol or glycerol, optionally mixed with minor amounts of water as described above.

In another aspect of the invention the liquid composition of the present invention is used for producing a solid dispersion of at least one active ingredient, such as a drug described further above, in at least one cellulose ether as described above and optionally one or more adjuvants. The solid dispersion is produced by removing the liquid diluent from the composition. One method of removing the liquid diluent from the liquid composition is by casting the liquid composition into a film or a capsule or by applying the liquid composition onto a solid carrier that in turn may comprise an active ingredient. A preferred method of producing the solid dispersion is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers'Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7-page 35, line 25.

Alternatively, the solid dispersion of the present invention may be prepared by i) blending a) at least one cellulose ether defined above, b) one or more active ingredients and c) one or more optional additives, and ii) subjecting the blend to melt-extrusion. The term "melt extrusion" as used herein includes processes known as injection molding, melt casting and compression molding. Techniques for melt-extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The above-mentioned components a), b) and optionally c) are preferably mixed in the form of particles, more preferably in powdered form. The components a), b) and optionally c) may be pre-mixed before feeding the blend into a device utilized for melt-extrusion. Useful devices for melt-extrusion, specifically useful extruders, are known in the art. Alternatively, the components a), b) and optionally c) may be fed separately into the extruder and blended in the device before or during a heating step. Preferably components a), b) and optionally c) are pre-blended in an extruder hopper and fed from there into the extruder. The composition or the components that has or have been fed into an extruder are passed through a heated area of the extruder at a temperature which will melt or soften the composition or at least one or more components thereof to form a blend throughout which the active ingredient is dispersed. The blend is subjected to melt-extrusion and caused to exit the extruder. Typical extrusion melt temperatures are from 50 to 210° C., preferably from 70 to 200° C., more preferably from 90 to 190° C., as determined by the setting for the extruder heating zone(s). An operating temperature range should be selected that will minimize the degradation or decomposition of the active ingredient and other components of the composition during processing. Single or multiple screw extruders, preferably twin screw extruders, can be used in the melt-extrusion process of the present invention. The molten or softened mixture obtained in the extruder are forced through one or more exit openings, such as one or more nozzles or dies. The molten or softened mixture then exits via a die or other such element having one or a plurality of openings, at which time, the melt-extruded blend (now called the extrudate) begins to harden. Since the extrudate is still warm or hot upon exiting the die, it may be easily shaped, molded, chopped, ground, spheronized into beads, cut into strands, tabletted or otherwise processed to the desired physical form.

By spray-drying or melt extrusion preferably a solid amorphous dispersion is produced wherein at least the major portion, more preferably at least 90 wt %, most preferably 100% of the active ingredient is in amorphous form and dispersed in the cellulose ether. The term "amorphous" as used herein means that the active ingredient does not have a long-range three-dimensional translational order. The solid dispersion of the present invention preferably comprises from 20 to 99.9 percent, more preferably from 30 to 98 percent, and most preferably from 60 to 95 percent of a cellulose ether a) as described above, and preferably from 0.1 to 80 percent, more preferably from 2 to 70 percent, and most preferably from 5 to 40 percent of an active ingredient b), based on the total weight of the cellulose ether a) and the active ingredient b). The combined amount of the cellulose ether a) and the active ingredient b) is preferably at least 70 percent, more preferably at least 80 percent, and most preferably at least 90 percent, based on the total weight of the solid dispersion. The remaining amount, if any, are one or more of the adjuvants c) as described above. The solid dispersion can comprise one or more of the cellulose ethers a), one or more of the active ingredients b), and optionally one or more of the adjuvants c), however their total amount is generally within the above-mentioned ranges.

Once the solid dispersion of at least one active ingredient in at least one cellulose ether has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms, such as tablets, pills, granules, pellets, caplets microparticles, fillings of capsules, or into pastes, creams, suspensions or slurries. The amount of the active ingredient in the dosage form is generally is at least 0.1 percent, preferably at least 1 percent, more preferably at least 3 percent, most preferably at least 5 percent and generally up to 70 percent, preferably up to 50 percent, more preferably up to 30 percent, most preferably up to 25 percent, based on the total weight of the dosage form.

In another aspect of the invention the liquid composition of the present invention may be used for coating dosage forms, such as tablets, granules, pellets, caplets, lozenges, suppositories, pessaries or implantable dosage forms, to form a coated composition. If the liquid composition of the present invention comprises an active ingredient, such as a drug, drug layering can be achieved, i.e., the dosage form and the coating may comprise different active ingredients for different end-uses and/or having different release kinetics.

In yet another aspect of the invention the liquid composition of the present invention may be used for the manufacture of capsules in a process which comprises the step of contacting the liquid composition with dipping pins.

The liquid composition and the solid dispersion of the present invention may further comprise optional additives, such as coloring agents, pigments, opacifiers, flavor and taste improvers, antioxidants, plasticizers, surfactants, lubricants, anti-tack agents, glidants, fillers, disintegrants, binders, salts, such as sodium chloride; saccharides, such as white sugar and lactose; a second cellulose ether, and any combination thereof. Useful amounts and types of one or more optional adjuvants are generally known in the art and depend on the intended end-use of the liquid composition or the solid dispersion of the present invention. A large variety of optional adjuvants is disclosed in International Patent Application WO 2005/115330, page 45, line 20-page 46, line 33.

The following examples are for illustrative purposes only and are not intended to limit the scope of the present invention. All percentages are by weight unless otherwise specified.

EXAMPLES 1 to 3 and COMPARATIVE EXAMPLES A to H

The determination of the % methoxyl and % hydroxypropoxyl in hydroxypropyl methylcellulose is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion.

The viscosity of the samples is measured as a 2% by weight aqueous solution at 20° C. according to ASTM D2363-79 (Reapproved 2006).

Determination of s23/s26

The determination of ether substituents in cellulose ethers is generally known and e.g., described in Carbohydrate Research, 176 (1988) 137-144, Elsevier Science Publishers B.V., Amsterdam, DISTRIBUTION OF SUBSTITUENTS IN O-ETHYL-O-(2-HYDROXYETHYL)CELLULOSE by Bengt Lindberg, Ulf Lindquist, and Olle Stenberg.

Specifically, determination of s23/s26 is conducted as follows:

10-12 mg of the cellulose ether are dissolved in 4.0 mL of dry analytical grade dimethyl sulfoxide (DMSO) (Merck, Darmstadt, Germany, stored over 0.3 nm molecular sieve beads) at about 90° C. under stirring and then cooled down to room temperature again. The solution is left stirring at room temperature over night to ensure complete solubilization. The entire reaction including the solubilization of the cellulose ether is performed using a dry nitrogen atmosphere in a 4 mL screw cap vial. After solubilization the dissolved cellulose ether is transferred to a 22 mL screw cap vial. Powdered sodium hydroxide (freshly pestled, analytical grade, Merck, Darmstadt, Germany) and ethyl iodide (for synthesis, stabilized with silver, Merck-Schuchardt, Hohenbrunn, Germany) in a thirty fold molar excess of the reagents sodium hydroxide and ethyl iodide per hydroxyl group of the anhydroglucose unit are added and the solution is vigorously stirred under nitrogen in the dark for three days at ambient temperature. The perethylation is repeated with addition of the threefold amount of the reagents sodium hydroxide and ethyl iodide compared to the first reagent addition and further stirring at room temperature for additional two days. Optionally the reaction mixture can be diluted with up to 1.5 mL DMSO to ensure good mixing during the course of the reaction. 5 mL of 5% aqueous sodium thiosulfate solution is poured into the reaction mixture and the obtained solution is then extracted three times with 4 mL of dichloromethane. The combined extracts are washed three times with 2 mL of water. The organic phase is dried with anhydrous sodium sulfate (ca. 1 g). After filtration the solvent is removed in a gentle stream of nitrogen and the sample is stored at 4° C. until further sample preparation.

Hydrolysis of about 5 mg of the perethylated samples is performed under nitrogen in a 2 mL screw cap vial with 1 mL of 90% aqueous formic acid under stirring at 100° C. for 1 hour. The acid is removed in a stream of nitrogen at 35-40° C. and the hydrolysis is repeated with 1 mL of 2M aqueous trifluoroacetic acid for 3 hours at 120° C. in an inert nitrogen atmosphere under stirring. After completion the acid is removed to dryness in a stream of nitrogen at ambient temperature using ca. 1 mL of toluene for co-distillation.

The residues of the hydrolysis are reduced with 0.5 mL of 0.5 M sodium borodeuteride in 2N aqueous ammonia solution (freshly prepared) for 3 hours at room temperature under stirring. The excess reagent is destroyed by drop wise addition of ca. 200 μL of concentrated acetic acid. The resulting solution is evaporated to dryness in a stream of nitrogen at ca. 35-40° C. and subsequently dried in vacuum for 15 min at room temperature. The viscous residue is dissolved in 0.5 mL of 15% acetic acid in methanol and evaporated to dryness at room temperature. This is done five times and repeated four times with pure methanol. After the final evaporation the sample is dried in vacuum overnight at room temperature.

The residue of the reduction is acetylated with 600 μL of acetic anhydride and 150 μL of pyridine for 3 hrs at 90° C. After cooling the sample vial is filled with toluene and evaporated to dryness in a stream of nitrogen at room temperature. The residue is dissolved in 4 mL of dichloromethane and poured into 2 mL of water and extracted with 2 mL of dichloromethane. The extraction is repeated three times. The combined extracts are washed three times with 4 mL of water and dried with anhydrous sodium sulfate. The dried dichloromethane extract is subsequently submitted to GC analysis. Depending on the sensitivity of the GC system, a further dilution of the extract can be necessary.

Gas-liquid (GLC) chromatographic analyses are performed with Hewlett Packard 5890A and 5890A Series II type of gas chromatographs equipped with J&W capillary columns DB5, 30 m, 0.25 mm ID, 0.25 μm phase layer thickness operated with 1.5 bar helium carrier gas. The gas chromatograph is programmed with a temperature profile that holds constant at 60° C. for 1 min, heats up at a rate of 20° C./min to 200° C., heats further up with a rate of 4° C./min to 250° C., heats further up with a rate of 20° C./min to 310° C. where it is held constant for another 10 min. The injector temperature is set to 280° C. and the temperature of the flame ionization detector (FID) is set to 300° C. 1 μL of the samples is injected in the splitless mode at 0.5 min valve time. Data are acquired and processed with a LabSystems Atlas work station.

Quantitative monomer composition data are obtained from the peak areas measured by GLC with FID detection. Molar responses of the monomers are calculated in line with the effective carbon number (ECN) concept but modified as described in the table below. The effective carbon number (ECN) concept has been described by Ackman (R. G. Ackman, J. Gas Chromatogr., 2 (1964) 173-179 and R. F. Addison, R. G. Ackman, J. Gas Chromatogr., 6 (1968) 135-138) and applied to the quantitative analysis of partially alkylated alditol acetates by Sweet et. al (D. P. Sweet, R. H. Shapiro, P. Albersheim, Carbohyd. Res., 40 (1975) 217-225).

ECN increments used for ECN calculations:

| Type of carbon atom | ECN increment |
| --- | --- |
| hydrocarbon | 100 |
| primary alcohol | 55 |
| secondary alcohol | 45 |

In order to correct for the different molar responses of the monomers, the peak areas are multiplied by molar response factors MRFmonomer which are defined as the response relative to the 2,3,6-Me monomer. The 2,3,6-Me monomer is chosen as reference since it is present in all samples analyzed in the determination of s23/s26. MRFmonomer=ECN2,3,6-Me/ECNmonomer The mole fractions of the monomers are calculated by dividing the corrected peak areas by the total corrected peak area according to the following formulas:

$$s23=[(23\text{-Me}+23\text{-Me-6-HAMe}+23\text{-Me-6-HA}+23\text{-Me-6-HAHAMe}+23\text{-Me-6-HAHA}];$$

and $$s26=[(26\text{-Me}+26\text{-Me-3-HAMe}+26\text{-Me-3-HA}+26\text{-Me-3-HAHAMe}+26\text{-Me-3-HAHA}],$$

wherein s23 is the sum of the molar fractions of anhydroglucose units which meet the following conditions:
a) the two hydroxy groups in the 2- and 3-positions of the anhydroglucose unit are substituted with methyl groups and the 6-position is not substituted (=23-Me);
b) the two hydroxy groups in the 2- and 3-positions of the anhydroglucose unit are substituted with methyl groups and the 6-position is substituted with methylated hydroxyalkyl (=23-Me-6-HAMe) or with a methylated side chain comprising 2 hydroxyalkyl groups (=23-Me-6-HAHAMe); and
c) the two hydroxy groups in the 2- and 3-positions of the anhydroglucose unit are substituted with methyl groups and the 6-position is substituted with hydroxyalkyl (=23-Me-6-HA) or with a side chain comprising 2 hydroxyalkyl groups (=23-Me-6-HAHA). s26 is the sum of the molar fractions of anhydroglucose units which meet the following conditions:
a) the two hydroxy groups in the 2- and 6-positions of the anhydroglucose unit are substituted with methyl groups and the 3-position is not substituted (=26-Me);
b) the two hydroxy groups in the 2- and 6-positions of the anhydroglucose unit are substituted with methyl groups and the 3-position is substituted with methylated hydroxyalkyl (=26-Me-3-HAMe) or with a methylated side chain comprising 2 hydroxyalkyl groups (=26-Me-3-HAHAMe); and
c) the two hydroxy groups in the 2- and 6-positions of the anhydroglucose unit are substituted with methyl groups and the 3-position is substituted with hydroxyalkyl (=26-Me-3-HA) or with a side chain comprising 2 hydroxyalkyl groups (=26-Me-3-HAHA).

The results of the determination of the substituents in the HAMC are listed in Table 4 below. In the case of HPMC's hydroxyalkyl (HA) is hydroxypropyl (HP) and methylated hydroxyalkyl (HAMe) is methylated hydroxypropyl (HPMe).

Example 1

Hydroxypropyl methylcellulose (HPMC) was produced according to the following procedure. Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 2.0 mole of sodium hydroxide per mole of anhydroglucose units in the cellulose and the temperature was adjusted to 40° C. After stiffing the mixture of aqueous sodium hydroxide solution and cellulose for about 30 minutes at 40° C., 1.5 mole of dimethyl ether, 2.5 mole of methyl chloride and 0.5 mole of propylene oxide per mole of anhydroglucose units were added to the reactor. The contents of the reactor were then heated in 60 min to 80° C. After having reached 80° C., the first stage reaction was allowed to proceed for 5 min.

The contents of the reactor were further heated at 80° C. for 20 min. Then the second stage of the reaction was started by addition of methyl chloride in an amount of 2.8 molar equivalents of methyl chloride per mole of anhydroglucose units. The addition time for methyl chloride was 10 min. Then a 50 weight percent aqueous solution of sodium hydroxide at an amount of 2.3 mole of sodium hydroxide per mole of anhydroglucose units was added over a time period of 50 min. The rate of addition was 0.046 mole of sodium hydroxide per mole of anhydroglucose units per minute. After the second stage addition was completed the contents of the reactor were kept at a temperature of 80° C. for further 135 min.

After the reaction the reactor was vented and cooled down to about 50° C. The contents of the reactor were removed and transferred to a tank containing hot water. The crude HPMC was then neutralized with formic acid and washed chloride free with hot water (assessed by $AgNO_3$ flocculation test), cooled to room temperature and dried at 55° C. in an air-swept drier. The material was then ground using an Alpine UPZ mill using a 0.5 mm screen.

The obtained powder was partially depolymerized in a known manner by heating the powderous samples with up to 3.0 g gaseous hydrogen chloride per kg of powder at a temperature of at most 85° C. until the desired viscosity was achieved. The partially depolymerized hydroxypropyl methylcellulose was neutralized with sodium bicarbonate.

Example 2

Example 1 was repeated, except that the temperature and dosage profile for the second stage was changed. After the first stage was finished by allowing to proceed for 5 min at 80° C., the contents of the reactor were further cooled down to 65° C. within 20 min. Then the second stage of the reaction was started by addition of methyl chloride in an amount of 2.8 molar equivalents of methyl chloride per mole of anhydroglucose units. The addition time for methyl chloride was 10 min. Then a 50 weight percent aqueous solution of sodium hydroxide at an amount of 2.3 mole of sodium hydroxide per mole of anhydroglucose units was added over a time period of 45 min. The rate of addition was 0.051 mole of sodium hydroxide per mole of anhydroglucose units per minute. After the second stage addition was completed the contents of the reactor were heated up to 80° C. in 20 min and then kept at a temperature of 80° C. for 135 min.

After the reaction the reactor was vented and cooled down to about 50° C. The contents of the reactor were removed and further processed as described in Example 1. The obtained powder was partially depolymerized and subsequently neutralized in a known manner as generally described in Example 1.

Example 3

Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 2.0 mole of sodium hydroxide per mole of anhydroglucose units in the cellulose and the temperature was adjusted to 40° C. After stiffing the mixture of aqueous sodium hydroxide solution and cellulose for about 20 minutes at 40° C., 1.5 mole of dimethyl ether, 2.5 mole of methyl chloride and 1.15 mole of propylene oxide per mole of anhydroglucose units were added to the reactor. The contents of the reactor were then heated in 60 min to 80° C. After having reached 80° C., the first stage reaction was allowed to proceed for 15 min.

The second stage of the reaction was started by addition of methyl chloride in an amount of 2.8 molar equivalents of methyl chloride per mole of anhydroglucose units. The addition time for methyl chloride was 10 min. Then a 50 weight percent aqueous solution of sodium hydroxide at an amount of 2.3 mole of sodium hydroxide per mole of anhydroglucose units was added over a time period of 90 min. The rate of addition was 0.026 mole of sodium hydroxide per mole of anhydroglucose units per minute. After the second stage addition was completed the contents of the reactor were kept at a temperature of 80° C. for 120 min.

After the reaction the reactor was vented and cooled down to about 50° C. The contents of the reactor were removed and further processed as described in Example 1. The obtained powder was partially depolymerized and subsequently neutralized in a known manner as generally described in Example 1.

Comparative Example A (Not Prior Art)

Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 1.8 mole of sodium hydroxide per mole of anhydroglucose units in the cellulose and the temperature was adjusted to 40° C. After stiffing the mixture of aqueous sodium hydroxide solution and cellulose for about 30 minutes at 40° C., 1.5 mole of dimethyl ether, 2.3 mole of methyl chloride and 0.7 mole of propylene oxide per mole of anhydroglucose units were added to the reactor. The contents of the reactor were then heated in 60 min to 80° C. After having reached 80° C., the first stage reaction was allowed to proceed for 5 min.

The contents of the reactor were then cooled to 60° C. within 20 min. The second stage of the reaction was started by addition of methyl chloride in an amount of 2.5 molar equivalents of methyl chloride per mole of anhydroglucose units. The addition time for methyl chloride was 10 min. Then a 50 weight percent aqueous solution of sodium hydroxide at an amount of 2.0 mole of sodium hydroxide per mole of anhydroglucose units was added over a time period of 45 min. The rate of addition was 0.044 mole of sodium hydroxide per mole of anhydroglucose units per minute. After the second stage addition was completed the contents of the reactor were heated up to 80° C. in 30 min and then kept at a temperature of 80° C. for 135 min.

After the reaction the reactor was vented and cooled down to about 50° C. The contents of the reactor were removed and further processed as described in Example 1. The obtained powder was partially depolymerized and subsequently neutralized in a known manner as generally described in Example 1.

Comparative Example B (Not Prior Art)

Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 3.0 mole of sodium hydroxide per mole of anhydroglucose units in the cellulose and the temperature was adjusted to 40° C. After stiffing the mixture of aqueous sodium hydroxide solution and cellulose for about 30 minutes at 40° C., 1.5 mole of dimethyl ether, 5.0 mole of methyl chloride and 1.0 mole of propylene oxide per mole of anhydroglucose units were added to the reactor. The contents of the reactor were then heated in 60 min to 80° C. After having reached 80° C., the first stage reaction was allowed to proceed for 25 min.

Then the reaction was cooled down to 60° C. within 20 min. Then a 50 weight percent aqueous solution of sodium hydroxide at an amount of 1.00 mole of sodium hydroxide per mole of anhydroglucose units was added over a time period of 60 min. The rate of addition was 0.017 mole of sodium hydroxide per mole of anhydroglucose units per minute. After the second stage addition was completed, the contents of the reactor were heated up to 80° C. within 20 min and then kept at a temperature of 80° C. for 120 min.

After the reaction the reactor was vented and cooled down to about 50° C. The contents of the reactor were removed and further processed as described in Example 1. The obtained powder was partially depolymerized and subsequently neutralized in a known manner as generally described in Example 1.

Comparative Example C (Not Prior Art)

Comparative Example B was repeated, except that the amount of propylene oxide added to the reaction mixture was 1.6 mole of propylene oxide per mole of anhydroglucose units. The obtained powder was partially depolymerized and subsequently neutralized in a known manner as generally described in Example 1.

Comparative Example D (Not Prior Art)

Example 1 was repeated, except that the temperature and dosage profile for the second stage was changed. After the first stage was finished by allowing to proceed for 5 min at 80° C., the contents of the reactor were further cooled down to 50° C. within 20 min. Then the second stage of the reaction was started by addition of methyl chloride in an amount of 2.8 molar equivalents of methyl chloride per mole of anhydroglucose units. The addition time for methyl chloride was 10 min. Then a 50 weight percent aqueous solution of sodium hydroxide at an amount of 2.3 mole of sodium hydroxide per mole of anhydroglucose units was added over a time period of 15 min. The rate of addition was 0.153 mole of sodium hydroxide per mole of anhydroglucose units per minute. After the second stage addition was completed the contents of the reactor were heated up to 80° C. in 20 min and then kept at a temperature of 80° C. for 135 min.

After the reaction the reactor was vented and cooled down to about 50° C. The contents of the reactor were removed and further processed as described in Example 1. The obtained powder was partially depolymerized and subsequently neutralized in a known manner as generally described in Example 1.

Comparative Examples E-G

The HPMC's of Comparative Example E-G are commercially available from The Dow Chemical Company. Their properties are listed in Table 1 below.

Comparative Example H

Finely ground wood cellulose pulp was loaded into a jacketed, agitated reactor. The reactor is evacuated and purged with nitrogen to remove oxygen and then evacuated again. The reaction was carried out in one stage. A 50 weight percent aqueous solution of sodium hydroxide was sprayed onto the cellulose in an amount of 3.90 mole of sodium hydroxide per mole of anhydroglucose units in the cellulose and the temperature is adjusted to 40° C. After stirring the mixture of aqueous sodium hydroxide solution and cellulose for about 20 minutes at 40° C., 2.07 mole of dimethyl ether, 4.40 mole of methyl chloride and 1.00 mole of propylene oxide per mole of anhydroglucose units were added to the reactor. The contents of the reactor were then heated in 80 min to 80° C. After having reached 80° C., the reaction was allowed to proceed for 60 min.

After the reaction the reactor was vented and cooled down to about 50° C. The contents of the reactor were removed and further processed as described in Example 1. The obtained powder was partially depolymerized and subsequently neutralized in a known manner as generally described in Example 1.

The properties of the hydroxypropyl methyl celluloses (HPMCs) of Examples 1 to 3 and of Comparative Examples A and H are listed in Table 1 below. The details of determining s23/s26 and are listed in Table 2 below.

Liquid Organic Compositions 10 weight percent of the HPMC's of Examples 1-3 and of Comparative Examples A-H were diluted in I) a mixture of methanol/water having a weight ratio of 90/10 at room temperature, II) a mixture of methanol/water having a weight ratio of 90/10 and additionally comprising 0.4 wt.-% of NaOH, based on the total weight of the methanol/water mixture. Viscous liquid compositions were obtained in all cases.

Impact of Cellulose Ethers on the Aqueous Solubility of a Poorly Soluble Drug

The ability of the cellulose ethers of Examples 1 to 3 and of Comparative Examples A to H to maintain drug concentrations in an aqueous solution at supersaturation levels was tested with the poorly water soluble drugs Griseofulvin and Phenyloin.

Griseofulvin has a water solubility of 8.54 mg/l, a log P of 2.2, a Tm of 220° C., a Tg of 85° C., and, accordingly a Tm/Tg=493° K/358° K=1.39. [Feng, Tao et. al.; J. Pharm. Sci.; Vol. 97, No. 8, 2008, pg 3207-3221 and W. Curatolo, Pharmaceutical Research, Vol. 26, No. 6, June 2009, pg 1422]. Griseofulvin belongs to group 2 on the map Tm/Tg ratio versus log P (FIG. 14 on page 1018 in MOLECULAR PHARMACEUTICS VOL. 5, NO. 6).

Phenyloin has a water solubility of 32 mg/l, a log P of 2.47, a Tm of 295° C., a Tg of 71° C. and, accordingly a Tm/Tg=568° K/344° K=1.65 [Friesen et al., MOLECULAR PHARMACEUTICS VOL. 5, NO. 6, 1003-1019 and W. Curatolo, Pharmaceutical Research, Vol. 26, No. 6, June 2009, pg 1422]. Phenyloin belongs to group 3 on the map Tm/Tg ratio versus log P (FIG. 14 on page 1018 in MOLECULAR PHARMACEUTICS VOL. 5, NO. 6, 2008).

Solutions of a cellulose ether listed in Table 1 below (950 µl, 3.16 mg/L) in phosphate buffered saline (82 mM sodium chloride, 20 mM sodium phosphate dibasic, 47 mM potassium phosphate monobasic, 0.5 wt % simulated intestinal fluid powder, pH 6.5) at 37° C. were robotically delivered into designated 1 mL vials arranged in an aluminum 96 (8 ×12) well block heated to 37° C. using a Tecan 150 liquid handler. Organic drug solutions at 37° C. were dispensed onto the phosphate buffered saline aqueous solution comprising a cellulose ether listed in Table 1 below. The organic drug solution was a) 20 g/L griseofulvin in dimethylformamide, 50 µL, final maximum drug concentration of 1000 mg/L, or b) 20 g/L phenyloin in dimethylformamide, 50 µL, final maximum drug concentration of 1000 mg/L The robot aspirated and dispensed liquid in a set sequence for each vial for about 30 s to mix. After 180 minutes the vials were centrifuged 1 min at about 3200×g (g=gravitational force on earth). An aliquot (30 µl) was transferred to methanol (150 µl) in a 96-well plate, sealed, briefly gently agitated to mix, and then the drug concentration was analyzed by HPLC.

In a Control Run the experiment was repeated with a phosphate buffered saline aqueous solution which did not contain any amount of cellulose ether.

In Table 1 below the concentrations of Griseofulvin and Phenyloin are listed that have not precipitated upon centrifugation after 180 minutes but that remain dissolved in the phosphate buffered saline aqueous solution.

The results in Table 1 below illustrate that the cellulose ethers comprised in the liquid compositions and in the solid dispersions of the present invention are able to maintain the concentration of poorly water-soluble drugs in an aqueous solution at supersaturation levels. A considerably higher drug concentration in an aqueous solution can be maintained than in the Control Run in the absence of a cellulose ether.

It has surprisingly been found that for some drugs the above-described cellulose ethers wherein s23/s26 is 0.29 or less even have a higher ability to keep the drug at supersaturation levels in an aqueous solution than comparable cellulose ethers wherein s23/s26 is more than 0.29. For example the drug Griseofulvin, which has a very low water solubility of 8.54 mg/l and belongs to group 2 on the map Tm/Tg ratio versus log P (FIG. 14 on page 1018 in MOLECULAR PHARMACEUTICS VOL. 5, NO. 6, 2008) has a higher concentration in the presence of the cellulose ethers of Examples 1-3 than in the presence of Comparative Examples A to H.

TABLE 1

| (Comparative) Example | DS (methyl) | MS (hydroxypropyl) | Viscosity at 20° C. [mPa · s]¹⁾ | s23/s26 | Griseofulvin concentration [mg/L] at 180 min. | Phenytoin concentration [mg/L] at 180 min. |
|---|---|---|---|---|---|---|
| 1 | 1.83 | 0.19 | 4.8 | 0.22 | 912 | 295 |
| 2 | 1.96 | 0.17 | 5.0 | 0.25 | 825 | 306 |
| 3 | 1.84 | 0.39 | 6.0 | 0.27 | 878 | 243 |
| A (Comparative)* | 1.93 | 0.29 | 3.4 | 0.30 | 676 | 291 |
| B (Comparative)* | 1.92 | 0.20 | 4.4 | 0.31 | 770 | 298 |
| C (Comparative)* | 1.93 | 0.35 | 4.1 | 0.32 | 566 | 249 |
| D (Comparative)* | 2.01 | 0.18 | 5.1 | 0.34 | 700 | 278 |
| E (Comparative) | 1.84 | 0.25 | 3.1 | 0.40 | 658 | 296 |
| -F (Comparative) | 1.97 | 0.27 | 4.3 | 0.47 | 593 | 293 |
| G (Comparative) | 1.84 | 0.16 | 4.1 | 0.41 | 789 | 296 |
| H (Comparative)* | 1.83 | 0.19 | 3.1 | 0.43 | 631 | 259 |
| Control | — | — | — | — | 130 | 68 |

¹⁾measured as 2.0 weight percent aqueous solution
*Not prior art

TABLE 2

| | (HPMC) | | | | | | | | | | |
|---|---|---|---|---|---|---|---|---|---|---|---|
| (Comparative) Example | 1 | 2 | 3 | A | B | C | D | E | F | G | H |
| DS (USP) | 1.83 | 1.96 | 1.84 | 1.93 | 1.92 | 1.93 | 2.01 | 1.84 | 1.97 | 1.84 | 1.83 |
| MS (USP) | 0.19 | 0.17 | 0.39 | 0.29 | 0.2 | 0.35 | 0.18 | 0.25 | 0.27 | 0.16 | 0.19 |
| mol fraction (26-Me) | 0.2873 | 0.2828 | 0.2374 | 0.2451 | 0.2621 | 0.2452 | 0.2534 | 0.2218 | 0.2081 | 0.2310 | 0.2236 |
| mol fraction (26-Me-3-HA) | 0.0161 | 0.0131 | 0.0316 | 0.0237 | 0.0145 | 0.0201 | 0.0126 | 0.0175 | 0.0046 | 0.0139 | 0.0162 |
| mol fraction (26-Me-3-HAHA) | 0.0000 | 0.0000 | 0.0000 | 0.0000 | 0.0000 | 0.0000 | 0.0000 | 0.0000 | 0.0000 | 0.0000 | 0.0000 |
| mol fraction (26-Me-3HAMe) | 0.0025 | 0.0023 | 0.0020 | 0.0040 | 0.0021 | 0.0031 | 0.0032 | 0.0039 | 0.0043 | 0.0025 | 0.0026 |
| mol fraction (26-Me-3HAHAMe) | 0.0000 | 0.0000 | 0.0000 | 0.0000 | 0.0000 | 0.0000 | 0.0000 | 0.0000 | 0.0000 | 0.0000 | 0.0000 |
| mol fraction (23-Me) | 0.0587 | 0.0669 | 0.0522 | 0.0659 | 0.0748 | 0.0697 | 0.0815 | 0.0828 | 0.0907 | 0.0932 | 0.0933 |
| mol fraction (23-Me-6-HA) | 0.0094 | 0.0090 | 0.0202 | 0.0157 | 0.0109 | 0.0158 | 0.0094 | 0.0136 | 0.0109 | 0.0090 | 0.0109 |
| mol fraction (23-Me-6-HAHA) | 0.0000 | 0.0000 | 0.0000 | 0.0000 | 0.0000 | 0.0000 | 0.0000 | 0.0000 | 0.0000 | 0.0000 | 0.0000 |
| mol fraction (23-Me-6-HAMe) | 0.0000 | 0.0000 | 0.0000 | 0.0000 | 0.0000 | 0.0000 | 0.0000 | 0.0000 | 0.0000 | 0.0000 | 0.0000 |
| mol fraction (23-Me-6-HAHAMe) | 0.0000 | 0.0000 | 0.0000 | 0.0000 | 0.0000 | 0.0000 | 0.0000 | 0.0000 | 0.0000 | 0.0000 | 0.0000 |
| s23/s26 | 0.22 | 0.25 | 0.27 | 0.30 | 0.31 | 0.32 | 0.34 | 0.40 | 0.47 | 0.41 | 0.43 |

What is claimed is:

1. A liquid composition comprising an organic diluent and at least one cellulose ether having anhydroglucose units joined by 1-4 linkages and having methyl groups, hydroxyalkyl groups, and optionally alkyl groups being different from methyl as substituents such that
   hydroxyl groups of anhydroglucose units are substituted with methyl groups such that s23/s26 is 0.29 or less,
   wherein s23 is the molar fraction of anhydroglucose units wherein only the two hydroxyl groups in the 2- and 3-positions of the anhydroglucose unit are substituted with a methyl group and
   wherein s26 is the molar fraction of anhydroglucose units wherein only the two hydroxyl groups in the 2- and 6-positions of the anhydroglucose unit are substituted with a methyl group.

2. The liquid composition of claim 1 additionally comprising at least one active ingredient and optionally one or more adjuvants.

3. The liquid composition of claim 1 wherein said at least one cellulose ether has an MS (hydroxyalkyl) of 0.05 to 0.55.

4. The liquid composition of claim 1 wherein said at least one cellulose ether has a degree of the methyl substitution, DS(methyl), of 1.6 to 2.5.

5. The liquid composition of claim 1 wherein the sum of the MS(hydroxyalkyl) and the DS(methyl) is at least 1.8.

6. The liquid composition of claim 1 wherein said at least one cellulose ether has a viscosity of from 2.4 to 200 mPa·s, measured as a 2 wt.-% solution in water at 20° C. according to ASTM D2363 -79 (Reapproved 2006).

7. The liquid composition of claim 1 wherein said at least one cellulose ether is a hydroxypropyl methylcellulose and s23/s26 is 0.24 or less.

8. The liquid composition of claim 1 wherein the composition additionally comprises water and the composition comprises more than 50 weight percent of an organic diluent and less than 50 weight percent of water, based on the total weight of organic diluent and water.

9. A solid dispersion of at least one active ingredient in at least one cellulose ether having anhydroglucose units joined by 1-4 linkages and having methyl groups, hydroxyalkyl groups, and optionally alkyl groups being different from methyl as substituents such that hydroxyl groups of anhydroglucose units are substituted with methyl groups such that s23/s26 is 0.29 or less, wherein s23 is the molar fraction of anhydroglucose units wherein only the two hydroxyl groups in the 2- and 3-positions of the anhydroglucose unit are substituted with a methyl group and wherein s26 is the molar fraction of anhydroglucose units wherein only the two hydroxyl groups in the 2- and 6-positions of the anhydroglucose unit are substituted with a methyl group and wherein the active ingredient has an aqueous solubility of up to 40 mg/mL.

10. The solid dispersion of claim 9 that has been prepared by spray-drying a liquid composition comprising an organic diluent, said at least one active ingredient and said at least one cellulose ether.

11. The solid dispersion of claim 10 wherein the solid dispersion has been formulated into pellets, granules, pills, tablets, caplets, capsules microparticles, fillings of capsules or into a powder, paste, cream, suspension or slurry.

12. The solid dispersion of claim 9 that has been prepared by blending and melt-extruding said at least one active ingredient and said at least one cellulose ether.

13. The solid dispersion of claim 12 wherein the solid dispersion has been formulated into pellets, granules, pills, tablets, caplets, capsules microparticles, fillings of capsules or into a powder, paste, cream, suspension or slurry.

14. The solid dispersion of claim 9 wherein the active ingredient has an aqueous solubility of up to 2 mg/mL.

15. The solid dispersion of claim 9 wherein the active ingredient is a low solubility drug having a minimum aqueous solubility at a pH of 1 to 8 of 0.5 mg/mL or less.

16. A process for coating a dosage form comprising the step of contacting the liquid composition of claim 1 with the dosage form.

17. A process for the manufacture of capsules comprising the step of contacting the liquid composition of claim 1 with dipping pins.

* * * * *